US009332951B2

(12) United States Patent
Inglese et al.

(10) Patent No.: US 9,332,951 B2
(45) Date of Patent: May 10, 2016

(54) ALIGNMENT APPARATUS FOR DENTAL INTRAORAL RADIOLOGY

(75) Inventors: Jean-Marc Inglese, Bussy-Saint-Georges (FR); Sylvie Bothorel, Paris (FR)

(73) Assignee: TROPHY, Marne la Vallee (FR)

( * ) Notice: Subject to any disclaimer, the term of this patent is extended or adjusted under 35 U.S.C. 154(b) by 96 days.

(21) Appl. No.: 13/696,607

(22) PCT Filed: May 12, 2010

(86) PCT No.: PCT/IB2010/001422
§ 371 (c)(1),
(2), (4) Date: Nov. 7, 2012

(87) PCT Pub. No.: WO2011/141763
PCT Pub. Date: Nov. 17, 2011

(65) Prior Publication Data
US 2013/0051528 A1 Feb. 28, 2013

(51) Int. Cl.
A61B 6/08 (2006.01)
A61B 6/14 (2006.01)
(Continued)

(52) U.S. Cl.
CPC . *A61B 6/145* (2013.01); *A61B 6/08* (2013.01); *A61B 6/4494* (2013.01); *A61B 6/547* (2013.01); *A61B 6/587* (2013.01); *G03B 21/00* (2013.01); *G03B 42/042* (2013.01); *G03B 42/047* (2013.01)

(58) Field of Classification Search
CPC ............ A61B 6/08; A61B 6/14; A61B 6/145; A61B 6/547; A61B 6/587; A61B 6/4405; A61B 6/4494; G03B 21/00

USPC ............. 378/38, 62, 98, 98.8, 165, 166, 168, 378/170, 171, 173, 178, 181, 182, 191, 205, 378/206, 207
See application file for complete search history.

(56) References Cited

U.S. PATENT DOCUMENTS

| 4,012,638 A | 3/1977 | Altschuler et al. | |
| 4,907,251 A * | 3/1990 | Mork et al. | 378/39 |

(Continued)

FOREIGN PATENT DOCUMENTS

| JP | 2007-029353 | 2/2007 |
| WO | WO00/064223 | 10/2000 |

(Continued)

OTHER PUBLICATIONS

International Search Report for International Application No. PCT/IB2010/001422 mailed on Jan. 21, 2011, 4 pages.

*Primary Examiner* — Glen Kao
*Assistant Examiner* — Chic-Cheng Kao

(57) ABSTRACT

An apparatus for obtaining an intraoral x-ray image from a patient has an x-ray source and an intraoral image detector comprising one or more detectable elements. One or more sensors are positionally coupled near the x-ray source and are energizable to sense the location of the one or more detectable elements when the intraoral image detector is within the patient's mouth. A control logic processor is in signal communication with the one or more sensors and is responsive to stored instructions for calculating a detector position of the intraoral image detector. A projector is positionally coupled to the x-ray source and is in signal communication with the control logic processor and is energizable to project an image toward the calculated intraoral image detector position in response to signals from the control logic processor.

16 Claims, 7 Drawing Sheets

(51) Int. Cl.
 *A61B 6/00* (2006.01)
 *G03B 21/00* (2006.01)
 *G03B 42/04* (2006.01)

(56) References Cited

U.S. PATENT DOCUMENTS

| | | | |
|---|---|---|---|
| 5,212,720 | A | 5/1993 | Landi et al. |
| 5,463,669 | A | 10/1995 | Kaplan |
| 5,629,972 | A | 5/1997 | Hausmann et al. |
| 5,810,841 | A | 9/1998 | McNeirney et al. |
| 5,828,722 | A * | 10/1998 | Ploetz et al. .................. 378/38 |
| 6,447,164 | B1 * | 9/2002 | Polkus .......................... 378/206 |
| 6,594,090 | B2 * | 7/2003 | Kruschwitz et al. .......... 359/707 |
| 7,490,986 | B2 | 2/2009 | Takekoshi et al. |
| 7,567,752 | B2 * | 7/2009 | Klinghult et al. ............... 396/50 |
| 2006/0169288 | A1 * | 8/2006 | Kleen et al. .................... 128/845 |
| 2007/0025525 | A1 * | 2/2007 | Gilath ........................... 378/206 |
| 2008/0019579 | A1 * | 1/2008 | Crucs ........................... 382/128 |
| 2009/0060145 | A1 | 3/2009 | Tranchant et al. |
| 2009/0251709 | A1 | 10/2009 | Kindlein |
| 2010/0007725 | A1 | 1/2010 | Crucs |
| 2011/0249793 | A1 * | 10/2011 | Lalena et al. ................... 378/62 |

FOREIGN PATENT DOCUMENTS

| | | | | |
|---|---|---|---|---|
| WO | WO2004/017833 | | 3/2004 | |
| WO | WO 2006/061357 | * | 6/2006 | ............ A61B 6/00 |
| WO | WO2006/061357 | | 6/2006 | |
| WO | WO 2007/118990 | | 10/2007 | |
| WO | WO2007/149402 | | 12/2007 | |

* cited by examiner

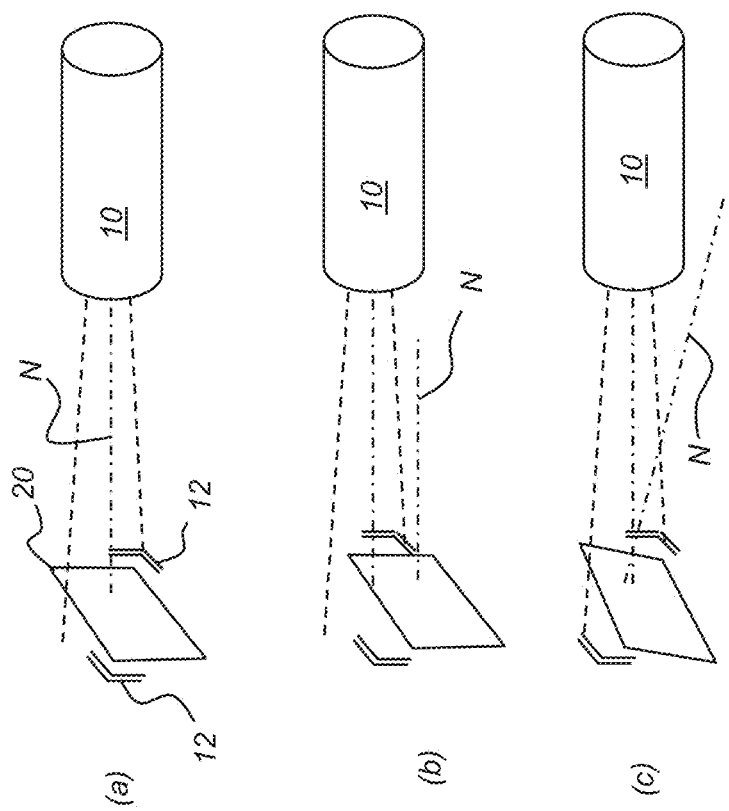

ALIGNMENT APPARATUS FOR DENTAL INTRAORAL RADIOLOGY

FIELD OF THE INVENTION

The invention relates generally to diagnostic imaging and more particularly to an apparatus for aligning an x-ray beam with an intra-oral image detector for dental radiography and an imaging system using such an apparatus.

BACKGROUND OF THE INVENTION

In conventional diagnostic radiography, an object is placed between an x-ray radiation source and a detector and the relative positions of the source and detector are positioned for proper alignment and angle for obtaining an image. When the object is an arm, leg, or chest of a patient, the x-ray tube and the detector are visible to the x-ray technician and can be easily aligned.

Alignment is more difficult for dental or intraoral radiography. The detector position is within the patient's mouth and is not visible to the technician. Instead, the technician typically places the detector into some type of holder, and then inserts the holder into place in the mouth. The holder may have a bite plate or other type of supporting member that helps to position the detector appropriately. As is well known, holders of this type can be cumbersome and uncomfortable to the patient. Holders and other positioning devices are not error-proof, and positioning errors with these devices can mean that the images obtained are not suitable for diagnosis. Poorly aligned detectors can be the cause of problems such as cone cuts, missed apices, and elongation and related angulation or parallax errors, for example. These alignment problems can result in re-takes, additional image captures to acquire an acceptable image. Re-takes are undesirable due to the additional x-ray radiation exposure to the patient and prolonged patient discomfort with the sensor in the mouth.

Conventional x-ray sources have included aim 1ndicators that help the technician adjust the position and angle of the x-ray source. Often these aim indicators use visible light to trace an outline that helps to center the radiation beam. These work well where the radiation detector can be seen, but fall short of what is needed where the detector is not visible, such as with intraoral imaging. The technician must guess or estimate both the position of the intraoral sensor and the angle of incidence of x-rays on the sensor.

The simplified schematic of FIGS. 1A and 1B show how mis-alignment between an x-ray source 10 and a detector 20 can occur. In these examples, x-ray source 10 provides visible light aim 1ndices 12 used for aim centering. When correct aim alignment is achieved, shown at example (a), detector 20 is centered, as shown within aim 1ndices 12. Aim 1s incorrect at examples (b) and (d).

For best imaging results, proper alignment with respect to angle, or angulation, is also needed. Incident radiation from x-ray source 10 is preferably orthogonal to detector 20 as shown in example (a). Line N in FIG. 1 indicates a normal, or orthogonal line, to the surface of detector 20. Examples (c) and (d) show incorrect angular alignment. In example (c), aim 1s correct but angulation is incorrect. In example (d), both aim and angulation are incorrect. In example (e), detector 20 is rotated in plane.

It is instructive to note that the schematic examples of FIGS. 1A and 1B assume an orthogonal positioning of x-ray source 10 to detector 20. In some embodiments, an oblique orientation may be used.

One proposed solution to the problem of positioning an intraoral sensor relative to the x-ray source is described in U.S. Patent Application Publication No. 2009/0060145 entitled "POSITIONING ADJUSTMENT OF A MOBILE RADIOLOGY FACILITY" by Tranchant et al. The apparatus described in Tranchant et al. '0145 uses an arrangement of electromagnetic emitters, such as radio frequency (RF) emitters, in cooperation with a sensor (reception unit) to determine the position and angle of an intraoral detector with respect to an x-ray source. Mis-alignment can then be reported to the operator on an operator console or display screen.

The solution proposed in the Tranchant et al. '0145 disclosure can detect and report mis-alignment for intraoral radiography and can minimize or eliminate the need to use cumbersome positioning devices within the patient's mouth. However, some practical difficulties remain. The technician needs information in order to correct for mis-alignment and to verify that proper alignment has been obtained. Conventional methods for reporting the alignment information, such as providing information on an operator console, for example, can be difficult to use when making position adjustments. The technician needs to move back and forth between the operator console and the x-ray tube, checking and correcting each adjustment until proper alignment is achieved.

Thus, there is a need for an apparatus and method for providing improved alignment of the radiation source and image detector in intraoral radiography.

SUMMARY OF THE INVENTION

An object of the present invention is to advance the art of intraoral radiography by providing apparatus and methods that improve the ability to align the radiation source and detector.

An advantage provided by the present invention is the rapid visualization of adjustment necessary to bring the radiation source and image detector into alignment.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an apparatus for obtaining an intraoral x-ray image comprising: a) an x-ray source; b) an intraoral image detector comprising one or more detectable elements; c) one or more sensors that are positionally coupled near the x-ray source and are energizable to sense the location of the one or more detectable elements when the intraoral image detector is within the patient's mouth; d) a control logic processor that is in signal communication with the one or more sensors and that is responsive to stored instructions for calculating a detector position of the intraoral image detector; and e) a projector that is positionally coupled to the x-ray source and that is in signal communication with the control logic processor and that is energizable to project an image toward the calculated intraoral image detector position in response to signals from the control logic processor.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 1A and 1B are simplified schematic block diagrams that show different aspects of the alignment problem.

DETAILED DESCRIPTION OF THE INVENTION

Figure 1B:
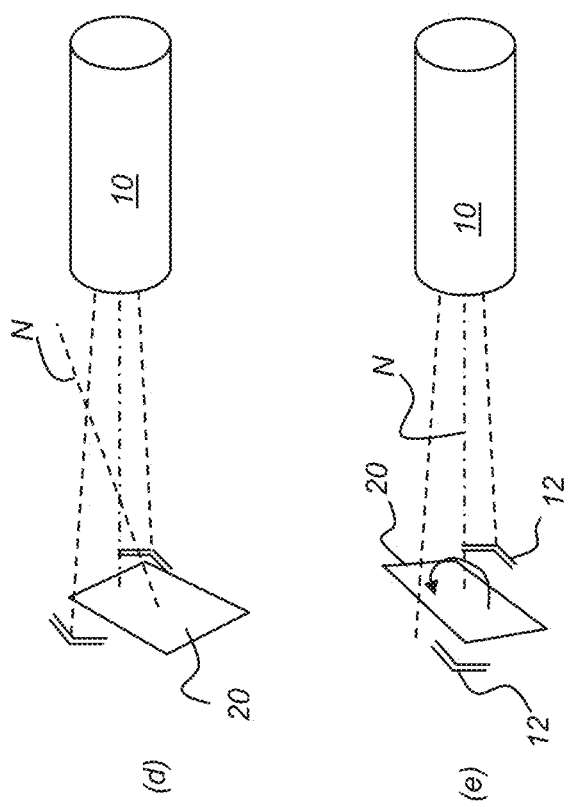

The following is a detailed description of the preferred embodiments of the invention, reference being made to the drawings in which the same reference numerals identify the same elements of structure in each of the several figures.

In the present disclosure, the term "detector" refers to the element that is placed in the patient's mouth, receives radiation, and provides the image content. Such a detector may be a photosensitive film element having a piece of film in a sleeve or film holder, wherein the film is separately developed to provide the x-ray image, a phosphor storage element that is separately scanned to provide x-ray image data, or a digital detector that provides the x-ray image data directly to an imaging system.

As the simplified schematic of FIGS. 1A and 1B showed, lateral (side-to-side) position of detector 20 and angulation of the detector 20 inside the patient's mouth are important factors for achieving good alignment. Rotation of the detector within its plane (that is, rotation about orthogonal axis N) as shown at (e) in FIG. 1B is less important, but can be a consideration for maintaining the desired alignment.

In order to better understand the parts and operation of the apparatus of the present invention, it is helpful to show how proper alignment can be detected by an imaging system. Referring to the block diagram of FIG. 2, there is shown an intraoral imaging apparatus 22 that detects alignment of imaging detector 20 with x-ray source 10. One example of such a system is given in the Tranchant et al. '0145 disclosure described previously.

Figure 2:
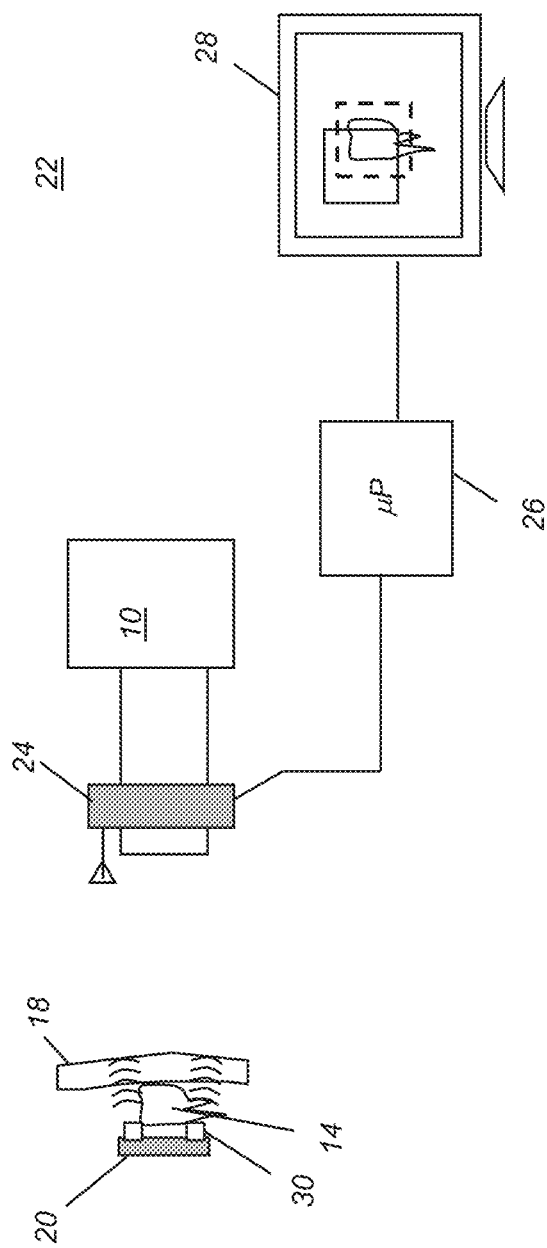
FIG. 2 is a schematic block diagram showing an imaging apparatus that calculates the lateral position and angular orientation of an intraoral image detector.

In the FIG. 2 arrangement, detector 20 is placed adjacent to a tooth 14, inside a cheek 18 of the patient. Incorporated as part of detector 20 are a number of detectable elements 30, which are shown as electromagnetic signal emitters, such as radio-frequency (RF) emitters. Detectable elements 30 are typically spaced apart from each other in order to provide triangulation information, as Tranchant et al. '0145 describes. A sensor 24, itself aligned and positionally coupled with x-ray source 10, senses the presence of detectable element 30 in some way, such as by sensing emitted RF signals. Methods for energizing and sensing RF emitters, such as the tiny emitters used in RFID tags, for example, are well known to those in the signal detection arts. A control logic processor 26, in signal communication with one or more sensors 24, employs conventional trigonometric calculations based on the received signals from, or other detectable features of, detectable elements 30 and the known position of sensor 24 with relation to x-ray source 10. This is performed in order to determine the corresponding positional and angular alignment of detector 20 in the patient's mouth relative to x-ray source 10. An operator console display 28 then indicates alignment information for the operator and may recommend the needed adjustment settings. Sensors 24 are energizable to receive electromagnetic signals of one or more predetermined frequencies.

Embodiments of the present invention improve upon the basic system of FIG. 2 by providing alignment information to the technician where it can be more easily used. The alignment apparatus of the present invention projects an image onto the cheek of the dental patient as a guide for proper alignment of the x-ray tube with respect to the position and angle of the detector. Referring to an embodiment of an imaging apparatus 36 in FIG. 3, control logic processor 26 obtains alignment information in similar manner to that described in FIG. 2. In addition, control logic processor 26 is also in image data signal communication with a projector 40 for projecting an image onto the patient's cheek 18, lips, or face.

Figure 4:
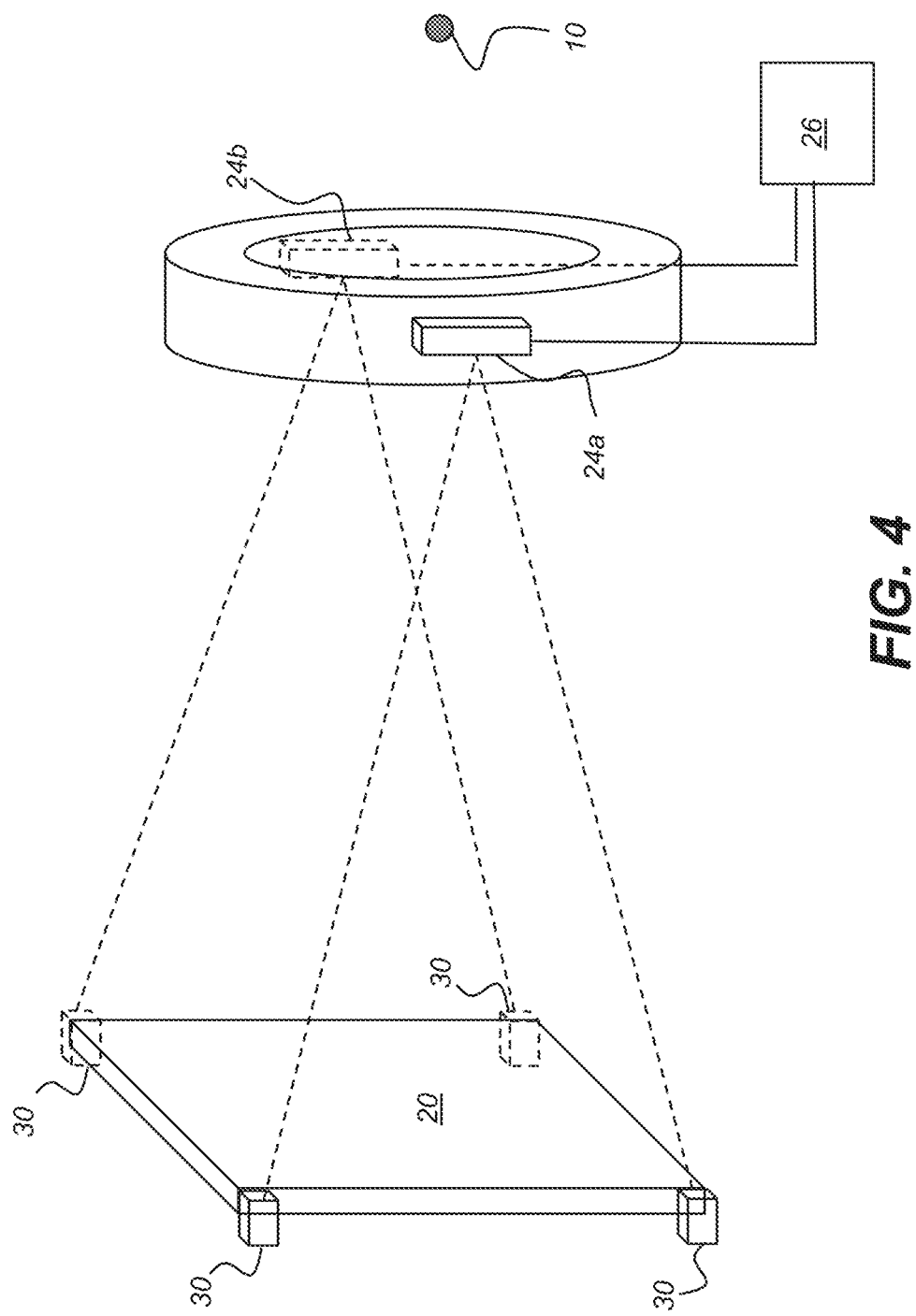
FIG. 4 is a schematic diagram that shows how triangulation is used for position detection in one embodiment of the present invention.

The perspective view of FIG. 4 shows, in schematic form, how triangulation is used to indicate position and angle of detector 20 in order to determine alignment offset in one embodiment. Sensors 24a and 24b, RF transceivers in one embodiment, are at a known position relative to the x-ray source 10, such as mounted near the x-ray source on the x-ray tube, for example. Signal emitters or other type of detectable elements 30 are typically disposed in pairs, positioned at corners of detector 20. Each detectable element 30 has a detectable feature that can be sensed by sensors 24a and 24b. In one embodiment, each detectable element 30 is an RF device that generates an electromagnetic field, such as in response to a transmitted signal from its corresponding signal receiver, sensors 24a or 24b. Phase, intensity, or other characteristic of the emitted electromagnetic field is measured at the corresponding sensors 24a and 24b, and is used in order to determine relative distance between emitting and receiving components. For the RF detection embodiment of FIG. 4, for example, when signals for each pair of emitters, acting as detectable elements 30, are in phase, good alignment has been achieved. An out-of-phase condition indicates poor alignment and can indicate the needed direction for adjustment. Sensors 24a and 24b are in signal communication with control logic processor 26.

In a similar manner, relative signal strength could alternately be used to indicate the position and angle of detector 20 with respect to the x-ray source for determining alignment offset. Using this approach in an RF embodiment, the nearest signal emitter acting as detectable element 30 has, correspondingly, the strongest intensity signal at sensor 24a or 24b. When the arrangement of FIG. 4 is used, signals of equal intensity emitted from all four emitters or other type of detectable element 30 indicate good alignment. When signal intensities vary, the pattern for their variation can be used to indicate which adjustments are needed. As one example, the Tranchant et al. '0145 disclosure, noted previously, describes a position detection system that uses triangulation and sensing of multiple emitted signals to compute alignment positioning. It can be appreciated that any of a number of different configurations can be used for determining proper alignment using one or more sensors 24 and detectable elements 30, as is well known to those skilled in the signal processing and position sensing arts.

Figure 5:
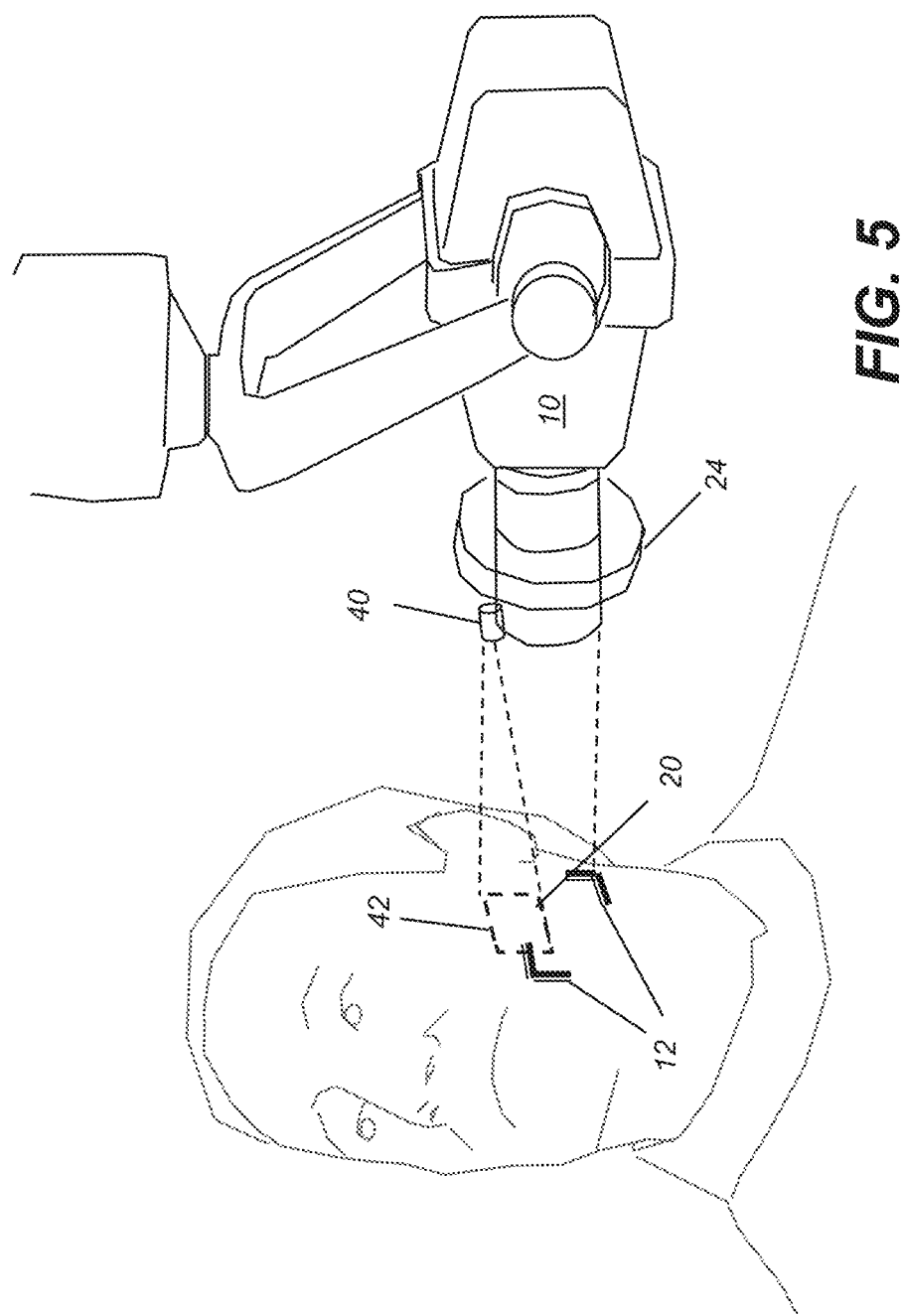
FIG. 5 is a perspective view showing an intraoral x-ray imaging apparatus according to one embodiment, in which alignment is not correct.
Figure 6:
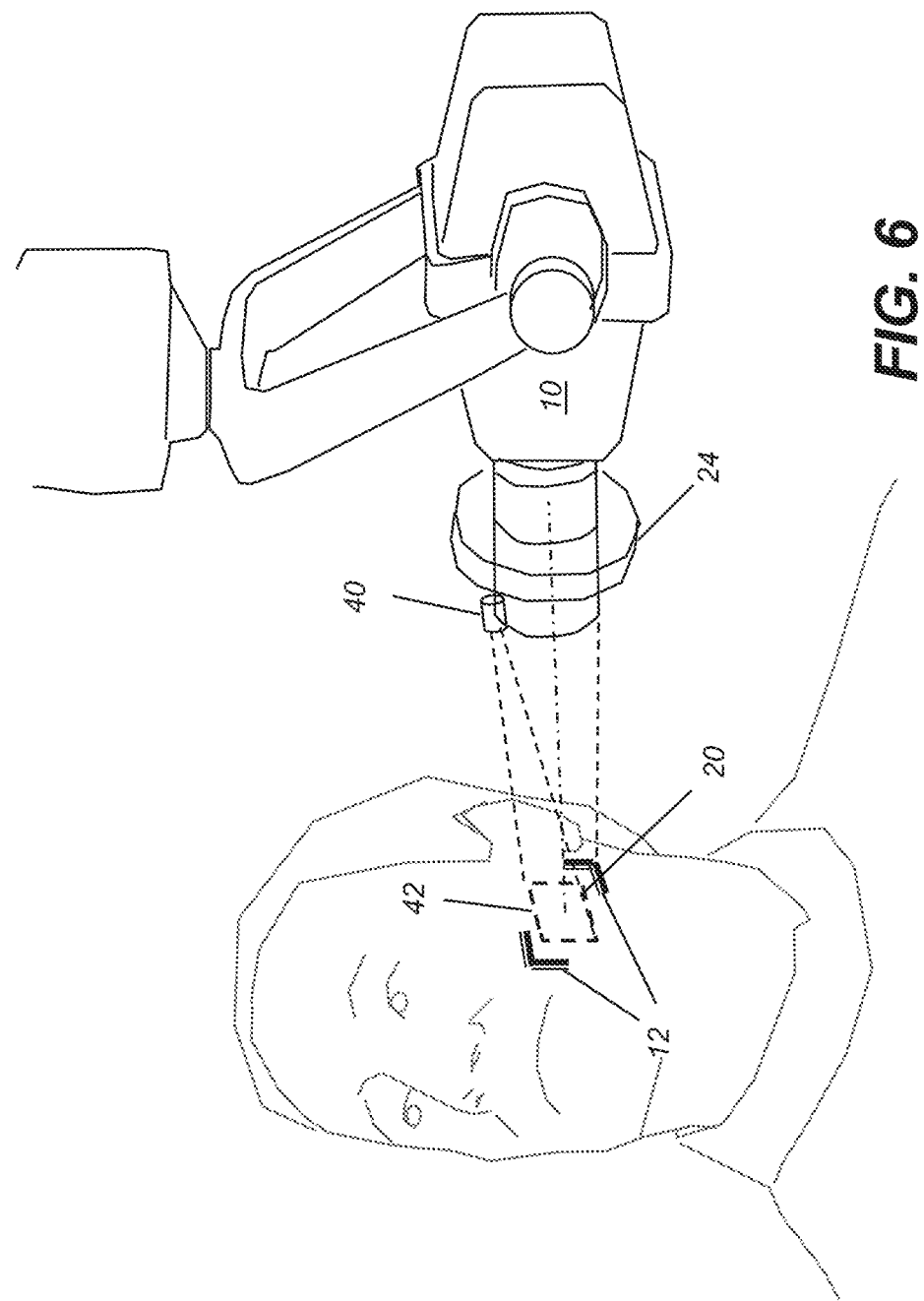
FIG. 6 is a perspective view showing an intraoral x-ray imaging apparatus according to one embodiment, in which alignment is correct.

Referring to the perspective views of FIGS. 5 and 6, the added advantage of embodiments of the present invention is shown. Projector 40, positionally coupled to x-ray source 10, such as mounted in position toward the end of the x-ray tube or on some other portion of the x-ray system, for example, projects a two-dimensional image onto the patient's cheek in order to indicate a position 42 of the concealed detector 20 (shown in dotted outline) and, unless already provided by the x-ray source 10, also to indicate the aim 1ndices 12 of the x-ray source. FIG. 5 shows an example in which aim alignment is incorrect, since position 42 is not aligned with aim 1ndices 12. FIG. 6 shows an example in which aim alignment is correct, with position 42 centered between aim 1ndices 12.

Projector 40 can be any of a number of types of imaging projector that can be mounted onto x-ray source 10. In one embodiment, projector 40 is a pico-projector, such as a Pico Projector Display from Microvision Inc., Redmond, Wash., USA, for example. Devices such as these are advantaged for a number of reasons, including small size, low weight, and low power requirements. These pico-projectors, used in cellphone and other highly portable electronic devices, scan one or more low-power lasers onto a display surface. The pico-projector requires a minimum of optical components for projection over a range of distances. The laser itself is turned on and off rapidly as needed, so that power is consumed only for those image pixels that are projected. This allows the pico-projector to operate at low power levels, so that battery power could be used for projector 40. Alternate embodiments use other types of electronic imaging projectors, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device.

Where lasers are used as illumination sources in projector 40, additional measures can be taken to minimize incidence of coherent laser light to the eyes of the patient or practitioner. Very low power lasers would be used, at scanning rates that deliver only a very small amount of light intensity at any point. A diffusive element may be provided in the light path, for example, to provide some scattering of the laser light, reducing intensity with little or no effect on the quality or utility of the projected image. Light-emitting diodes (LEDs) or other low-power solid-state light sources could alternately be used, such as organic LED (OLED) devices.

The image that is projected by projector 40 can take any of a number of forms and may include both aim 1ndicia 12 for the x-ray source and position 42 indicator for detector 20. Alternately, where aim 1ndicia 12 are already provided by the x-ray system, projector 40 may only provide a projection showing position 42. Because projector 40 employs a two-dimensional imaging device, the displayed image can have multiple parts and may include additional text fields, direction markers, and other elements. Position 42 may be shown in outline form, as shown in FIGS. 4 and 5, or may be represented in some other way. In one embodiment, the value of angular offset of detector 20 is indicated on the patient's cheek as a displayed numerical message. Alternately, animation or other capabilities of projector 40 could be used to provide additional position and angle information.

Color can be used to help indicate the relative amount of alignment offset in various ways. For example, even with the outline of detector 20 projected on the cheek surface, it can be difficult for the technician to know how to adjust for angular alignment. Display of indicia 12 and position 42 in different colors can help to guide the technician in adjusting the angle of the x-ray tube until both aim 1ndicia 12 and position 42 display in the same color, for example. Blinking of the display or of different portions of the displayed elements can also help to indicate and guide alignment adjustments. An audible beep may be provided to indicate acceptable or unacceptable alignment. Stationary indicators, such as arrows or target symbols can be projected onto the cheek of the patient. Animation can be provided to guide adjustment.

The invention has been described in detail with particular reference to a presently preferred embodiment, but it will be understood that variations and modifications can be effected within the spirit and scope of the invention. For example, control logic processor 26 (FIGS. 2-4) can be any of a number of types of logic processing device, including a computer or computer workstation, a dedicated host processor, a microprocessor, logic array, or other device that executes stored program logic instructions. Control logic processor 26 may also connect to detector 20 for obtaining an image and for controlling the operation of signal emitters 30. The electromagnetic signals emitted and detected for determining position can be any of a number of types of signal, such as RF signals in the 10 kHz-100 MHz range, for example.

Figure 3:
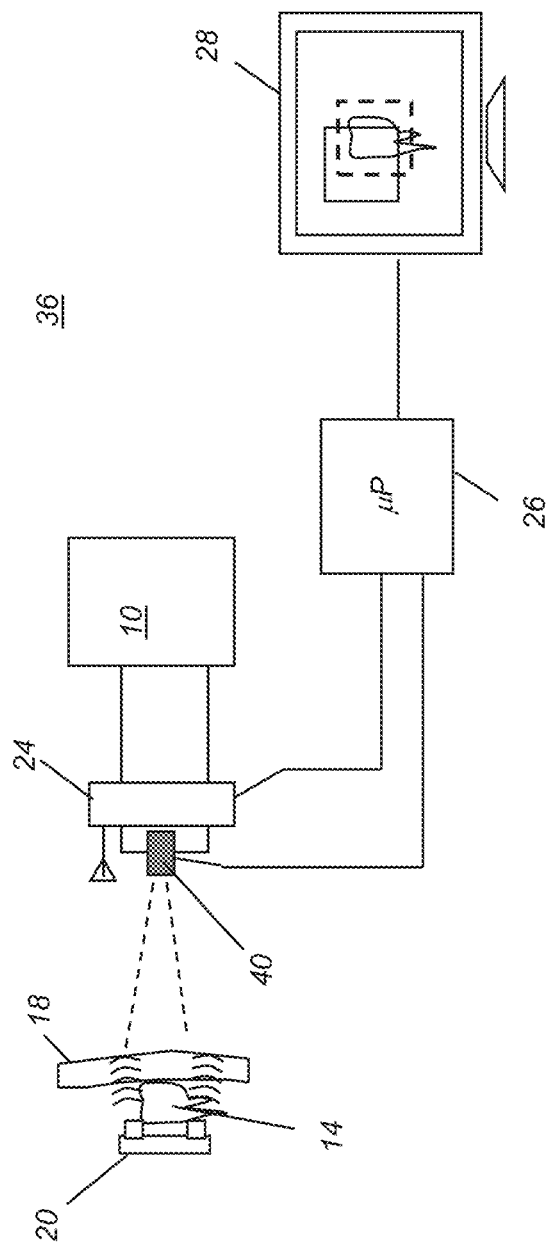
FIG. 3 is a schematic block diagram showing an imaging apparatus that calculates the lateral position and angular orientation of an intraoral image detector and projects a display onto the patient's cheek.

Embodiments shown and described with reference to FIGS. 2 and 3 showed use of radio frequency transmission and reception for identifying the position of intra-oral imaging detector 20. In such an embodiment, detectable element 30 is an RF emitter, such as an RFID device. Alternately, detectable element 30 can emit some other electromagnetic signal, such as light, for example. A bright light source from within the mouth may be perceptible to a sensor, particularly where the light is incident upon less dense tissue, such as the cheek. The light can be from within or outside of the visible spectrum. In yet another embodiment, ultrasound signals are emitted from detectable element 30 and sensed at sensor(s) 24. Yet another embodiment employs magnets as detectable elements 30 and uses magnetic attraction as a guide to determining the position and angular orientation of detector 20 within the patient's mouth.

The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. X-ray source
12. Aim 1ndex
14. Tooth
18. Cheek
20. Detector
22. Imaging apparatus
24, 24a, 24b. Sensor
26. Control logic processor
28. Display
30. Sensed element
36. Imaging apparatus
40. Projector
42. Position

What is claimed is:

1. An apparatus for obtaining an intraoral x-ray image from a patient, the apparatus comprising:
   an x-ray source;
   an intraoral image detector comprising one or more detectable elements;
   one or more sensors positionally coupled near the x-ray source and energizable to sense the location of the one or more detectable elements when the intraoral image detector is within the patient's mouth;

a control logic processor in signal communication with the one or more sensors and responsive to stored instructions for calculating a detector position of the intraoral image detector; and a projector positionally coupled to the x-ray source and in signal communication with the control logic processor and energizable to project a 2D image including aim indicia representative of position and angle information toward the calculated intraoral image detector position in response to signals from the control logic processor, where when a three-dimensional angle offset is caused between an optical axis of the x-ray source and a surface of the intraoral image detector, an image process for guiding resolution of the angle offset is executed for the projected image.

2. The apparatus of claim 1 wherein the intraoral image detector is taken from the group consisting of: a photosensitive film imaging device, a storage phosphor imaging device, and a digital detector device, and wherein the projected image is a color image.

3. The apparatus of claim 1 wherein the projector projects an image using laser illumination.

4. The apparatus of claim 1 wherein at least one of the one or more sensors is mounted on the x-ray source.

5. The apparatus of claim 1 wherein the one or more detectable elements emit an electromagnetic signal at radio-frequency.

6. The apparatus of claim 1 wherein the one or more detectable elements emit light.

7. The apparatus of claim 1 wherein the one or more detectable elements comprises a magnet.

8. The apparatus of claim 1 wherein the projector uses a digital micromirror array or a liquid crystal device.

9. The apparatus of claim 1, where the projector is adapted to provide position, alignment and angle information of the detector in the projected 2D image in response to signals from the control logic processor.

10. The apparatus of claim 9, where the projector is adapted to project the 2D image at least partially outside an x-ray radiation area.

11. The apparatus of claim 1 wherein the projected image varies in appearance according to an alignment offset between the x-ray source and the intraoral image detector.

12. A method for obtaining an intraoral x-ray image comprising:

emitting a plurality of signals from signal emitters associated with an intraoral image detector;

calculating the position of the intraoral image detector according to the emitted signals;

projecting a 2D image representative of position and angle information toward the calculated detector position, wherein projecting the image comprises projecting position, alignment and angle aim indicia of an x-ray source in the projected 2D image in response to signals from a control logic processor; and guiding resolution of a three-dimensional angle offset between an optical axis of the x-ray source and a surface of the intraoral image detector using the angle aim indicia in the projected 2D image.

13. The method of claim 12 wherein emitting the plurality of signals comprises emitting light or radio frequency signals.

14. The method of claim 12 wherein projecting the image comprises projecting an outline representative of the image detector.

15. The method of claim 12 wherein projecting the image comprises projecting an image representative of the image detector and further comprising using a color that indicates the relative amount of an alignment offset.

16. An apparatus for obtaining an intraoral x-ray image comprising:

an x-ray source;

an intraoral image detector comprising a plurality of signal emitters, wherein each signal emitter is energizable to emit an electromagnetic signal at one or more predetermined frequencies;

one or more signal receivers positionally coupled with the x-ray source and energizable to receive the electromagnetic signals from the signal emitters;

a control logic processor in signal communication with the one or more signal receivers and responsive to stored instructions for calculating a detector position of the intraoral image detector; and a projector positionally coupled to the x-ray source and in signal communication with the control logic processor and energizable to project a 2D image toward the calculated detector position in response to signals from the control logic processor, where when a three-dimensional angle offset is caused between an optical axis of the x-ray source and a surface of the intraoral image detector, an image process for guiding resolution of the angle offset is executed for the projected image.

* * * * *